US012773314B2

(12) United States Patent
Steenwyk

(10) Patent No.: US 12,773,314 B2
(45) Date of Patent: Oct. 27, 2026

(54) DELIVERY SYSTEM FOR SELF-EXPANDING VALVE WITH EXPOSED CUFF

(71) Applicant: St. Jude Medical, Cardiology Division, Inc., St. Paul, MN (US)

(72) Inventor: Nicholas Steenwyk, Minneapolis, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 559 days.

(21) Appl. No.: 18/473,594

(22) Filed: Sep. 25, 2023

(65) Prior Publication Data

US 2024/0156595 A1 May 16, 2024

Related U.S. Application Data

(60) Provisional application No. 63/383,991, filed on Nov. 16, 2022.

(51) Int. Cl.
*A61F 2/24* (2006.01)

(52) U.S. Cl.
CPC .......... *A61F 2/2436* (2013.01); *A61F 2/2418* (2013.01)

(58) Field of Classification Search
CPC .... A61F 2/2418; A61F 2/2433; A61F 2/2436; A61F 2/962; A61F 2002/9534; A61M 25/0067; A61M 25/003; A61M 25/008; A61M 25/2433; A61M 25/104
See application file for complete search history.

(56) References Cited

U.S. PATENT DOCUMENTS 6,858,034 B1 * 2/2005 Hijlkema .................. A61F 2/95 623/1.11
9,241,794 B2 1/2016 Braido
11,504,228 B2 11/2022 Braido
2002/0099435 A1 * 7/2002 Stinson ..................... A61F 2/97 623/1.12
2007/0219466 A1 * 9/2007 Tremulis ........... A61M 25/0082 600/585
2017/0348101 A1 * 12/2017 Vaughn ..................... A61F 2/95
2018/0055631 A1 3/2018 Morin
2018/0071089 A1 3/2018 Kaleta
2018/0153691 A1 * 6/2018 Anderson ............. A61F 2/2433
2018/0153693 A1 6/2018 Copeland
2019/0038409 A1 2/2019 Schraut
2019/0091013 A1 3/2019 Alkhatib
(Continued)

*Primary Examiner* — Christie Bahena
(74) *Attorney, Agent, or Firm* — SLEMAN & LUND LLP

(57) ABSTRACT

A prosthetic heart valve includes a self-expanding frame, a valve assembly, and an outer cuff. A delivery device includes an inner shaft, an outer shaft, and a distal sheath disposed about a portion of the inner shaft to form a compartment with the inner shaft. The inner shaft and the distal sheath may be axially translatable relative to one another. A distal tip may be disposed at a distal end of the delivery device. In a delivery condition of the system, the distal sheath may be in a distal-most position in which the distal sheath overlies portions of the prosthetic heart valve but a distal end of the distal sheath leaves the outer cuff uncovered. In the delivery condition, a gap distance may exist between the distal end of the distal sheath and a proximal end of the distal tip, the outer cuff being positioned along the gap distance.

20 Claims, 6 Drawing Sheets

(56) References Cited

U.S. PATENT DOCUMENTS

| | | | | |
|---|---|---|---|---|
| 2019/0117387 | A1 | 4/2019 | Li | |
| 2019/0117394 | A1 | 4/2019 | Morin | |
| 2019/0298968 | A1 | 10/2019 | Morin | |
| 2019/0365530 | A1* | 12/2019 | Hoang | A61F 2/2409 |
| 2020/0205967 | A1 | 7/2020 | Li | |
| 2022/0015902 | A1* | 1/2022 | Tegels | A61F 2/95 |

* cited by examiner

DELIVERY SYSTEM FOR SELF-EXPANDING VALVE WITH EXPOSED CUFF

CROSS-REFERENCE TO RELATED APPLICATIONS

This application claims the benefit of priority to the filing date of U.S. Provisional Patent Application No. 63/383,991, filed Nov. 16, 2022, the disclosure of which is hereby incorporated by reference herein.

BACKGROUND OF THE DISCLOSURE

The present disclosure relates to systems and methods for delivering and deploying a transcatheter prosthetic heart valve to a patient, particularly to the delivery and deployment of a transcatheter prosthetic heart valve with an outer sealing cuff.

Prosthetic heart valves that are collapsible to a relatively small circumferential size can be delivered into a patient less invasively than valves that are not collapsible. For example, a collapsible valve may be delivered into a patient via a tube-like delivery apparatus such as a catheter, a trocar, a laparoscopic instrument, or the like. This collapsibility can avoid the need for a more invasive procedure such as full open-chest, open-heart surgery.

Collapsible prosthetic heart valves typically take the form of a valve structure mounted on a stent. There are two types of stents on which the valve structures are ordinarily mounted: a self-expanding stent and a balloon-expandable stent. To place such valves into a delivery apparatus and ultimately into a patient, the valve must first be collapsed or crimped to reduce its circumferential size. Although the disclosure described herein is generally described in connection with a self-expanding prosthetic heart valve, the disclosure may also apply to otherwise similarly constructed balloon-expandable or otherwise expandable prosthetic heart valves.

Collapsible prosthetic heart valves, particularly self-expanding prosthetic heart valves, are typically maintained in the collapsed condition on a delivery device via an overlying sheath or capsule or tube as the prosthetic heart valve is delivered to a native heart valve for implantation (e.g., via a transfemoral route to the patient's aorta). When the prosthetic heart valve has reached the desired position, the overlying sheath is typically retracted in order to allow the prosthetic heart valve to expand into the implantation site. Because the overlying sheath radially overlaps (e.g., surrounds) the collapse prosthetic heart valve during delivery, the profile of the system at the location of the prosthetic heart valve is relatively large compared to a comparable system in which a sheath does not overlie the prosthetic heart valve during delivery (which may be the case for some balloon-expandable prosthetic heart valves). Because it is generally desirable to have a smaller profile system when delivering a prosthetic heart valve intravascularly (with all else being equal), it would be preferable to be able to have a prosthetic heart valve with a high-volume outer cuff that does not increase (or significantly increase) the size of the delivery system during delivery.

SUMMARY OF THE DISCLOSURE

According to one aspect of the disclosure, a delivery device for a collapsible prosthetic heart valve includes an inner shaft, an outer shaft, and a distal sheath disposed distal to the outer shaft and about a portion of the inner shaft to form a compartment with the inner shaft. The compartment may be sized to receive the prosthetic heart valve, and the inner shaft and the distal sheath may be axially translatable relative to one another. A distal tip may be disposed at a distal end of the delivery device. The distal sheath may be translatable between a proximal-most position and a distal-most position. The compartment may be completely exposed when the distal sheath is in the proximal-most position, and a gap distance may exist between a distal end of the distal sheath and a proximal end of the distal tip when the distal sheath is in the distal-most position. The distal tip may include a distal portion and a proximal portion, the distal portion having a rigidity that is less than a rigidity of the proximal portion. The proximal portion of the distal tip may be ring-shaped. The proximal portion of the distal tip may have an outer diameter that is equal to an outer diameter of the distal sheath. The proximal portion of the distal tip may have a wall thickness that is equal to a wall thickness of the distal sheath. A retainer may be positioned at a proximal end of the compartment, the retainer being configured to mate with retaining elements of the prosthetic heart valve. The distal tip may be axially fixed relative to the retainer. The distal tip may be axially translatable relative to the retainer.

According to another aspect of the disclosure, a prosthetic heart valve system may include a prosthetic heart valve and a delivery device. The prosthetic heart valve may include a self-expanding frame, a valve assembly mounted within the frame, and an outer cuff on an outer surface of the frame. The delivery device may include an inner shaft, an outer shaft, and a distal sheath disposed distal to the outer shaft and about a portion of the inner shaft to form a compartment with the inner shaft. The inner shaft and the distal sheath may be axially translatable relative to one another. A distal tip may be disposed at a distal end of the delivery device. The system may have a delivery condition in which the distal sheath is in a distal-most position in which the distal sheath overlies portions of the prosthetic heart valve but a distal end of the distal sheath leaves the outer cuff uncovered. In the delivery condition, a gap distance may exist between the distal end of the distal sheath and a proximal end of the distal tip, the outer cuff being positioned along the gap distance. The distal tip may include a distal portion and a proximal portion, the distal portion having a rigidity that is less than a rigidity of the proximal portion. The proximal portion of the distal tip may be ring-shaped. In the delivery condition of the system, a terminal inflow end of the prosthetic heart valve may be positioned within the proximal portion of the distal tip. The delivery device may include a retainer, and in the delivery condition of the system, retaining elements at an outflow end of the prosthetic heart valve may be coupled to the retainer. The distal tip may be axially fixed relative to the retainer. The distal tip may be axially translatable relative to the retainer.

According to a further aspect of the disclosure, a method of implanting a prosthetic heart valve into a patient may include transitioning a prosthetic heart valve into a collapsed delivery condition on a delivery device. The prosthetic heart valve may have a self-expanding frame, a valve assembly mounted within the frame, and an outer cuff on an outer surface of the frame. The method may include delivering the prosthetic heart valve into a vasculature of the patient while the prosthetic heart valve is in the collapsed delivery condition, the outer cuff of the prosthetic heart valve being uncovered by the delivery device during the delivering. The method may also include positioning the prosthetic heart valve within or adjacent to a native heart valve annulus while the prosthetic heart valve is in the collapsed delivery condition. While the prosthetic heart valve is positioned within or adjacent to the native heart valve annulus, a distal sheath of the delivery device may be retracted to allow the prosthetic heart valve to expand so that the outer cuff contacts that native valve annulus. The delivery device may include a distal tip positioned distally of the distal sheath, the distal tip including a proximal ring-shaped portion, and during the delivering, a terminal inflow end of the prosthetic heart valve is received within and constrained by the proximal ring-shaped portion of the distal tip. While the prosthetic heart valve is positioned within or adjacent to the native heart valve annulus, and before retracting the distal sheath, the distal tip may be advanced distally to uncover the terminal inflow end of the prosthetic heart valve.

DETAILED DESCRIPTION OF THE DISCLOSURE

Figure 1:
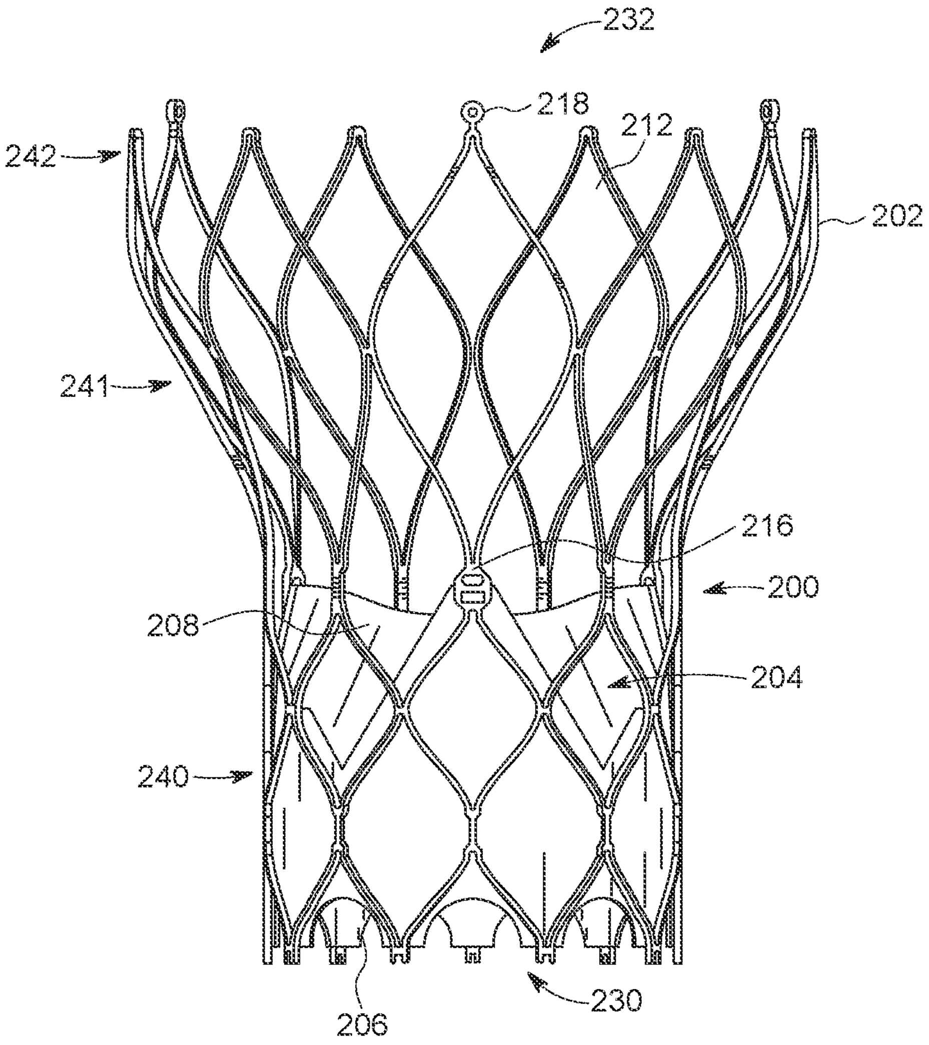
FIG. 1 (PRIOR ART)
FIG. 1 is a side elevational view of a collapsible prosthetic heart valve, according to the prior art, in an expanded condition, showing the valve assembly attached to the stent.

As used herein in connection with prosthetic heart valves, the term “inflow end” refers to the end of the heart valve through which blood first flows when implanted in an intended position and orientation, while the term “outflow end” refers to the opposite end, through which blood last flows when the prosthetic heart valve is implanted in the intended position and orientation. When used in connection with devices for delivering a prosthetic heart valve into a patient, the terms “proximal” and “distal” are to be taken as relative to the user of the delivery devices. In other words, in this context, “proximal” is to be understood as relatively close to the user of the delivery device, and “distal” is to be understood as relatively farther away from the user of the delivery device.

When a prosthetic heart valve is implanted within a native valve annulus, one potential reason for sub-optimal performance is perivalvular or paravalvular (“PV”) leak, which generally refers to leakage of blood (e.g., in the retrograde direction during diastole) between the outside of the prosthetic heart valve and the native tissue in which the prosthetic heart valve is implanted. PV leak typically has negative clinical ramifications, and thus reducing or eliminating PV leak is desirable. Transcatheter prosthetic heart valves may include PV leak mitigation features, such as an outer sealing skirt or cuff around the exterior of the stent (e.g., around the portion of the stent that engages the native annulus). These cuffs or skirts are typically intended to create a seal between the prosthesis and the native anatomy, which sometimes is highly calcified and irregular in its topography. Because of this, outer cuffs that fill greater volume (e.g., through means like active inflation, pile-knits, or filler fabrics/yarns) may be desirable to create an effective seal. However, high-volume cuffs, by definition, require more valve volume to be packed into the delivery system capsule compared to otherwise identical prosthetic heart valves with low-volume (or no) outer cuffs. Thus, a delivery device that houses a prosthetic heart valve with a high-volume outer cuff may require a larger profile at the location of the prosthetic heart valve during delivery compared to a prosthetic heart valve with a low-volume (or no) outer cuff. Because transcatheter prosthetic heart valves are typically delivered through the vasculature, space is limited and the largest profile of a delivery system housing the prosthetic heart valve during delivery may be an important factor. In fact, prosthetic heart valves with high-volume outer cuffs may have limited use if the corresponding enlargement of the profile of the delivery system is too large for patients with small access vessels. The disclosure provided herein may provide a delivery system that is capable of constraining a prosthetic heart valve with a high-volume cuff (e.g., a self-expanding prosthetic heart valve) but does not require a corresponding enlargement of the delivery device because the high-volume outer cuff is left partially or completely uncovered by the delivery device during delivery. This, in turn, may allow the outer cuff to fill space that would normally be occupied by the capsule (e.g., outer sheath) structure.

FIG. 1 shows a collapsible prosthetic heart valve 200 according to the prior art. The prosthetic heart valve 200 is designed to replace the function of a native aortic valve of a patient, although it should be understood that the concepts described herein may be applicable to the replacement of any native heart valve, including the mitral, tricuspid, or pulmonary heart valves. As discussed in detail below, the prosthetic heart valve has an expanded condition, shown in FIG. 1, and a collapsed condition.

Prosthetic heart valve 200 includes a collapsible and expandable stent 202 which may be formed from any biocompatible material, such as metals, metal alloys, synthetic polymers, or biopolymers capable of functioning as a stent. Stent 202 extends from an inflow or annulus end 230 to an outflow or aortic end 232 and includes an annulus section 240 adjacent to the inflow end and an aortic section 242 adjacent to the outflow end. The annulus section 240 has a relatively small cross-section in the expanded condition, while the aortic section 242 has a relatively large cross-section in the expanded condition. Preferably, annulus section 240 is in the form of a cylinder having a substantially constant diameter along its length. A transition section 241 may taper outwardly from the annulus section 240 to the aortic section 242. Each of the sections of the stent 202 may include a plurality of cells 212 connected to one another in one or more annular rows around the stent. For example, as shown in FIG. 1, the annulus section 240 may have two annular rows of complete cells 212 and the aortic section 242 and transition section 241 may each have one or more annular rows of partial cells 212. The cells 212 in the aortic section 242 may be larger than the cells 212 in the annulus section 240. The larger cells in the aortic section 242 better enable the prosthetic valve 200 to be positioned without the stent structure interfering with blood flow to the coronary arteries.

Stent 202 may include one or more retaining elements 218 at the outflow end 232 thereof, the retaining elements being sized and shaped to cooperate with female retaining structures provided on the deployment device. The engagement of retaining elements 218 with the female retaining structures on the deployment device helps maintain prosthetic heart valve 200 in assembled relationship with the deployment device, minimizes longitudinal movement of the prosthetic heart valve relative to the deployment device during unsheathing or resheathing procedures, and/or helps prevent rotation of the prosthetic heart valve 200 relative to the deployment device as the deployment device is advanced to the target location and during deployment.

The prosthetic heart valve 200 may include a valve assembly 204 positioned in the annulus section 240. Valve assembly 204 may include an inner cuff 206 and a plurality of leaflets 208 which collectively function as a one-way valve. The commissure between adjacent leaflets 208 may be connected to commissure features 216 on stent 202. Prosthetic heart valve 200 is shown in FIG. 1 with three leaflets 208, as well as three commissure features 216. As can be seen in FIG. 1, the commissure features 216 may lie at the intersection of four cells 212, two of the cells being adjacent to one another in the same annular row, and the other two cells being in different annular rows and lying in an end-to-end relationship. Preferably, commissure features 216 are positioned entirely within annulus section 240 or at the juncture of annulus section 240 and transition section 241. Commissure features 216 may include one or more eyelets that facilitate the suturing of the leaflet commissure to the stent. However, it should be appreciated that the prosthetic heart valves may have a greater or lesser number of leaflets and commissure features. For example, a prosthetic mitral valve may include two prosthetic leaflets with two commissures. Both the cuff 206 and the leaflets 208 may be wholly or partly formed of any suitable biological material or polymer.

In operation, a prosthetic heart valve, including the prosthetic heart valve described above, may be used to replace a native heart valve, such as the aortic valve, a surgical heart valve, or a heart valve that has undergone a surgical procedure. The prosthetic heart valve may be delivered to the desired site (e.g., near a native aortic annulus) using any suitable delivery device, including the delivery devices described in detail below. During delivery, the prosthetic heart valve is disposed inside the delivery device in the collapsed condition. The delivery device may be introduced into a patient using a transfemoral, transapical, or transseptal approach, although any transcatheter approach may be suitable. Once the delivery device has reached the target site, the user may deploy the prosthetic heart valve. Upon deployment, the prosthetic heart valve expands into secure engagement within the native aortic annulus. When the prosthetic heart valve is properly positioned inside the heart, it works as a one-way valve, allowing blood to flow in one direction and preventing blood from flowing in the opposite direction.

Figure 2:
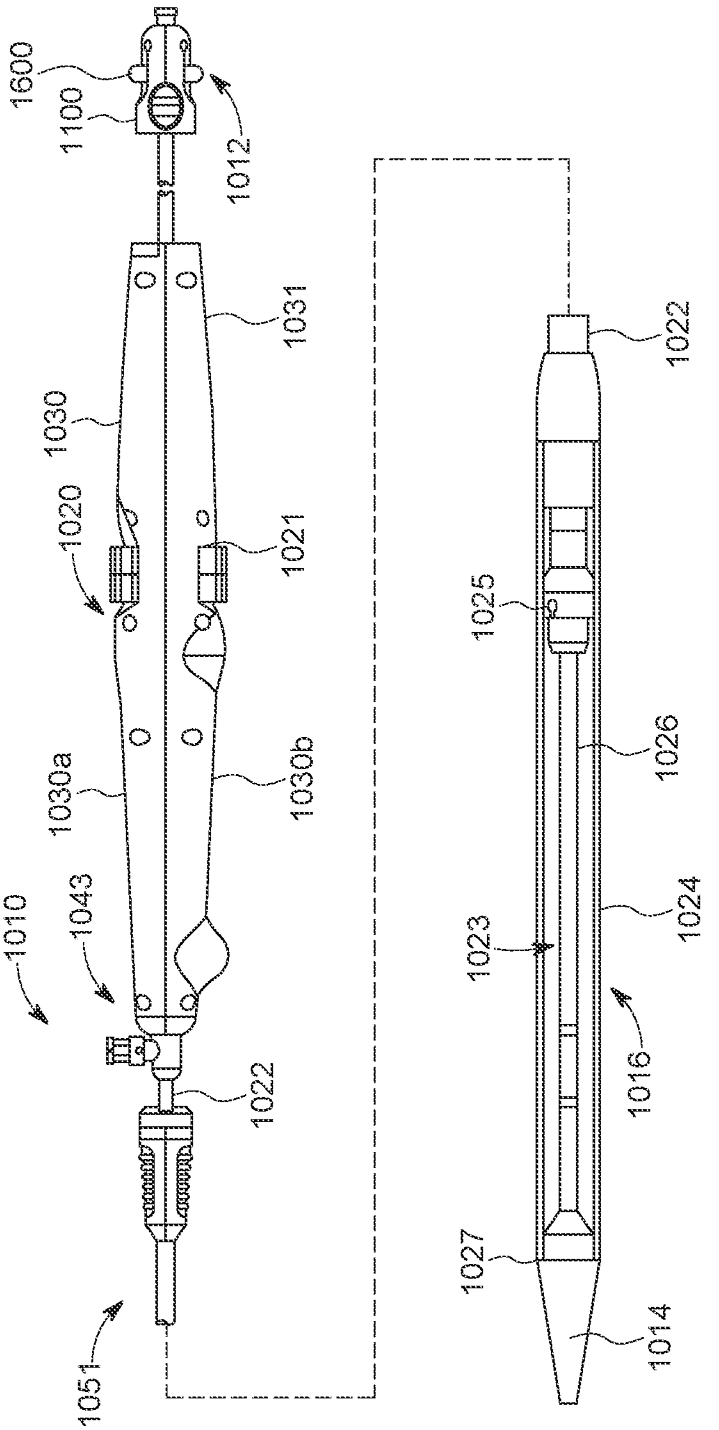
FIG. 2 (PRIOR ART)
FIG. 2 is side view of an operating handle for a transfemoral delivery device for a collapsible prosthetic heart valve, shown with a side elevational view of the distal portion of a transfemoral catheter assembly.

Turning now to FIG. 2, an exemplary prior art transfemoral delivery device 1010 for a collapsible prosthetic heart valve (or other types of self-expanding collapsible stents) has a catheter assembly 1016 for delivering the heart valve to and deploying the heart valve at a target location, and an operating handle 1020 for controlling deployment of the valve from the catheter assembly. The delivery device 1010 extends from a proximal end 1012 to a distal tip 1014. The catheter assembly 1016 is adapted to receive a collapsible prosthetic heart valve (not shown) in a compartment 1023 defined around an inner shaft 1026 and covered by a distal sheath 1024. The inner shaft 1026 extends through the operating handle 1020 to the distal tip 1014 of the delivery device and includes a retainer 1025 affixed thereto at a spaced distance from distal tip 1014 and adapted to hold a collapsible prosthetic valve in the compartment 1023.

The distal sheath 1024 surrounds the inner shaft 1026 and is slidable relative to the inner shaft such that it can selectively cover or uncover the compartment 1023. The distal sheath 1024 is affixed at its proximal end to an outer shaft 1022, the proximal end of which is connected to the operating handle 1020. The distal end 1027 of the distal sheath 1024 abuts the distal tip 1014 when the distal sheath fully covers the compartment 1023 and is spaced apart from the distal tip 1014 when the compartment 1023 is at least partially uncovered.

The operating handle 1020 is adapted to control the deployment of a prosthetic valve located in the compartment 1023 by permitting a user to selectively slide the outer shaft 1022 proximally or distally relative to the inner shaft 1026, or to slide the inner shaft 1026 relative to the outer shaft 1022, thereby respectively uncovering or covering the compartment with the distal sheath 1024. Operating handle 1020 includes frame 1030 which extends from a proximal end 1031 to a distal end and includes a top frame portion 1030*a* and a bottom frame portion 1030*b*. The proximal end of the inner shaft 1026 is coupled to a hub 1100, and the proximal end of the outer shaft 1022 is affixed to a carriage assembly within the frame 1030 that is slidable within the operating handle along a longitudinal axis of the frame 1030, such that a user can selectively slide the outer shaft relative to the inner shaft by sliding the carriage assembly relative to the frame. Alternatively, inner shaft 1026 may be actuated via hub 1100 to cover or uncover the compartment, for example for rapid covering or uncovering of the compartment 1023. Optionally, a stability sheath 1051 is disposed over some or all of the outer shaft 1022. The stability sheath 1051 may be attached to the outer shaft 1022 or may be unattached. Additionally, stability sheath 1051 may be disposed over a majority of outer shaft 1022 or over a minority of the outer shaft (e.g., over 49% or less, over 33%, etc.). Optionally, stability sheath 1051 may be more rigid than outer shaft 1022.

Additionally, hub 1100 may include a pair of buttons, each attached to a clip. These clips on hub 1100 may mate with voids on frame 1030 to ensure that the hub and the frame are securely coupled together. Optionally, hub 1100 may also include a wheel 1600 which may assist in reducing strain in the distal sheath 1024 when loading the prosthetic heart valve into the delivery device 1010.

A first mechanism for covering and uncovering the compartment 1023 will be referred to as a "fine" technique as covering and uncovering occur slowly with a high degree of precision. The "fine" movement may be provided by rotating a deployment wheel or actuator 1021, which may cause the carriage to pull or push the outer sheath 1022 (and thus the distal sheath 1024) proximally or distally. The second mechanism for covering and uncovering the compartment 1023 may be referred to as a "coarse" technique, by pulling or pushing the hub 1100 as described above. The "coarse" technique may be particularly suited for use when a prosthetic heart valve is not positioned within the compartment 1023. The delivery device may also include a resheathing lock 1043, which may restrict the motion of the distal sheath 1024 once the full deployment of the prosthetic heart valve is imminent. The resheathing lock 1043 may be disengaged when the desired position of the prosthetic heart valve is confirmed, so that the distal sheath 1024 may be further retracted to fully release the prosthetic heart valve. In other words, the resheathing lock 1043 may help prevent unintentional or premature complete deployment of the prosthetic heart valve. Additional features of the delivery device 1010, for example including the function of wheel 1600, are described in greater detail in U.S. Patent Publication No. 2018/0153693, the disclosure of which is hereby incorporated by reference herein.

Figure 3:
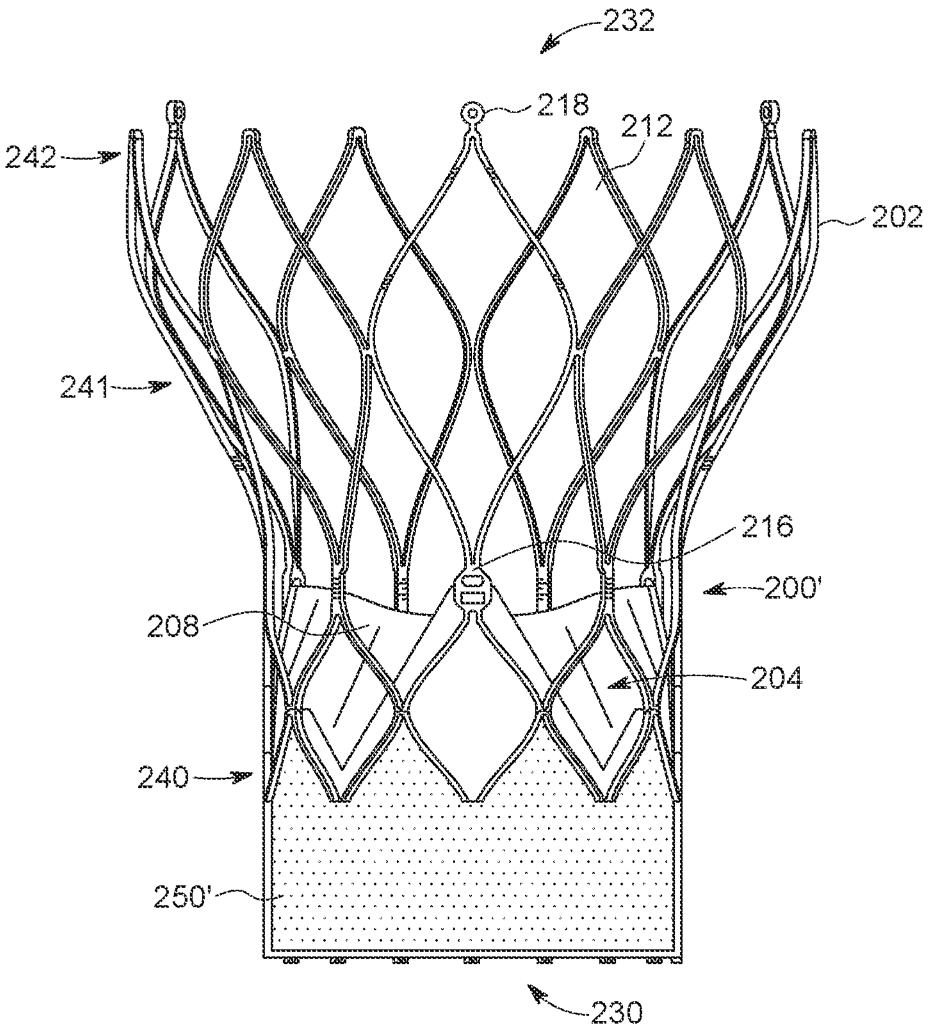
FIG. 3 is a side elevational view of the collapsible prosthetic heart valve of FIG. 1 with an added high-volume outer cuff.

The prosthetic heart valve 200 of FIG. 1 is shown with only an inner cuff 206 and no outer cuff. Prosthetic heart valve 200', shown in FIG. 3, may be identical to prosthetic heart valve 200 except that prosthetic heart valve 200' also includes an outer cuff 250' configured to mitigate or prevent PV leak. In the illustrated embodiment, outer cuff 250' is a high-volume outer cuff (e.g., a fabric that includes pile-knits or filler fabrics/yarns), which has a substantially straight inflow edge generally aligned with the inflow or annulus end 230 of the stent 202 and an outflow end that generally follows along the bottom struts of the second row of full cells 212 in the annulus section 240. However, it should be noted that the outflow end if the outer cuff 250' may have different heights and/or different shapes, including a generally straight outflow edge. For example, in one embodiment, the outflow edge of the outer cuff 250' may be straight and positioned at about the height of half of the longitudinal end-to-end distance of a cell 212 in the proximal-most row of cells. Preferably, the outer cuff 250' is positioned only at the annulus section 240 of the stent 202 because the intent of the outer cuff 250' is to contact the native valve annulus of the patient upon implantation. In the illustrated embodiment, a short distance of the terminal inflow end 230 of the stent 202 (e.g., at the apices of the cells 212 defining the inflow-most row of cells 212) is uncovered by the outer cuff 250'. In some embodiments, the inflow end 230 of the stent 202 may be entirely covered by the outer cuff 250', and in other embodiments a greater distance than shown in FIG. 3 may be uncovered. As is described below, an uncovered portion of the terminal inflow end 230 of the stent 202 may provide a particular use. However, it should be understood that the specifics of the outer cuff 250' shown in FIG. 3 and described herein are not critical to achieving the benefits provided by the delivery device described below, and various other configurations of outer cuffs for sealing against PV leak may work just as well with the delivery device described below. In fact, the delivery device disclosed below may even provide benefits for prosthetic heart valves that have "low-volume" outer cuffs.

Figure 4:
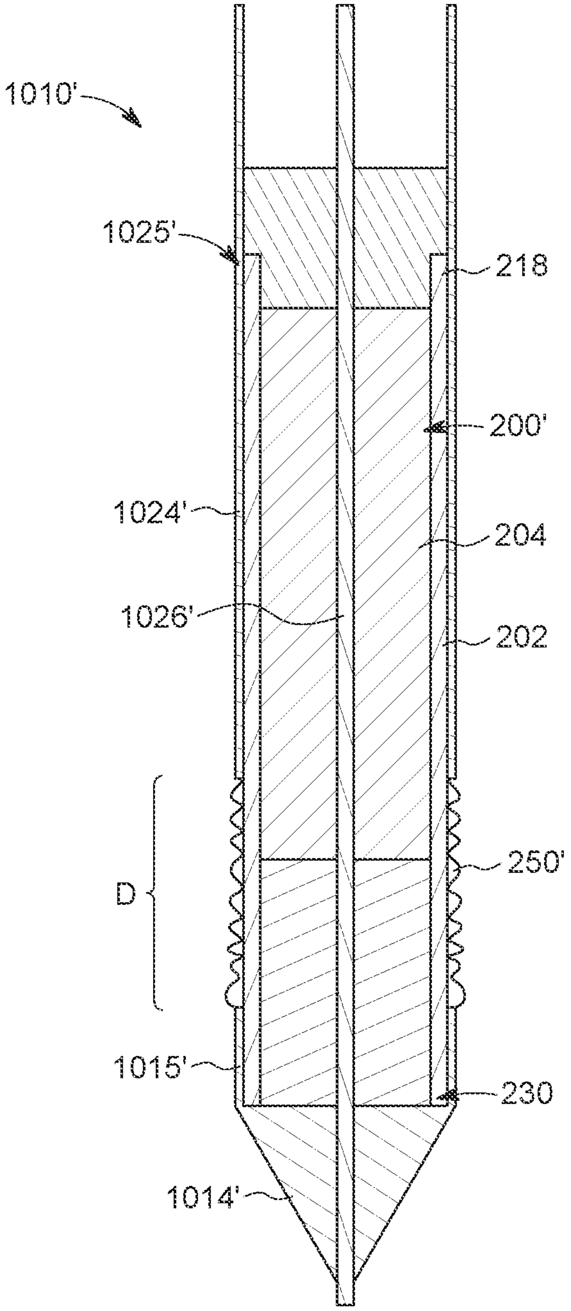
FIG. 4 is a highly schematic cross-section of a distal or leading end of a delivery device according to an aspect of the disclosure.

FIG. 4 shows a cross-section of the distal end of a delivery device 1010' according to an embodiment of the disclosure. Delivery device 1010' may be identical to delivery device 1010 described above, except for the differences described in connection with delivery device 1010'. In other words, components of delivery device 1010' that are not shown or described in connection with FIGS. 4-5D may be identical to the corresponding components of delivery device 1010. However, it should be understood that the components of delivery device 1010' that are not shown and described in connection with FIGS. 4-5D may be different than the specific configuration of the corresponding components of delivery device 1010, while still achieving the desired benefits (e.g., a different handle than is shown in delivery device 1010 may be used with delivery device 1010' without losing the desired effect).

The distal end of the delivery device 1010' is shown in FIG. 4, distal of the point at which an outer shaft (e.g., outer shaft 1022) transitions to (and/or is coupled to) the distal sheath 1024' which overlies the prosthetic heart valve 200' when the system is in the delivery condition shown in FIG. 4. The proximal portions of the delivery device 1010' visible in FIG. 4 may be generally similar to, or the same as, the delivery device 1010. For example, when in the delivery condition, the retaining elements 218 may be received within corresponding recesses in a retainer 1025', with the retaining elements 218 being prevented from radial expansion away from the retainer 1025' by virtue of the overlapping distal sheath 1024'. Also similar to delivery device 1010, delivery device 1010' includes an inner shaft 1026' around which the prosthetic heart valve 200' is positioned, the inner shaft 1026' and the distal sheath 1024' forming a compartment for receiving the prosthetic heart valve 200'.

One difference between delivery device 1010' and delivery device 1010 is that the distal sheath 1024' does not extend the entire distance into contact with the distal tip 1014'. In other words, even when the distal sheath 1024' is completely advanced to its distal-most position, a distance D exists between the distal end of the distal sheath 1024' and the proximal end of the distal tip 1014'. The distance D may be about equal to the axial length of the outer skirt 250' when the prosthetic heart valve 200' is in the collapsed condition. In some embodiments, the distal sheath 1024' may not be capable of advancing distally far enough to close the gap distance D. In other embodiments, the distal sheath 1024' may be capable of advancing distally far enough to close the gap distance D, but nonetheless distal sheath 1024' is positioned to have the gap distance D during delivery. In other words, when the prosthetic heart valve 200' is crimped or collapsed within the delivery device 1010' during delivery, the distal sheath 1024' does not cover any amount (or substantially any amount) of the outer cuff 250', nor any uncovered amount of the inflow end 230 of the stent 202. As can be seen in FIG. 4, by leaving the high-volume outer cuff 250' uncovered, the profile of the delivery device 1010', and particularly the inner diameter of the distal sheath 1024', does not need to be increased to accommodate the volume of the outer cuff 250'. Instead, the inner diameter of the distal sheath 1024' only needs to be larger enough to accommodate the uncovered portions of stent 202 positioned between the outflow end of the outer cuff 250' and the outflow end 232 of the stent 202. In FIG. 4, although a relatively large amount of distance is shown between the inflow end 230 of the stent 202 and the inflow end of the valve assembly 204, it should be understood that the valve assembly 204 may extend all the way (or nearly all the way) to the inflow end 230 of the stent 202.

Referring still to FIG. 4, if the inflow end 230 of the stent 202 were completely uncovered by any structure, it may tend to self-expand. This would typically be undesirable because, if the inflow end 230 of the stent expanded to a profile larger than the profile of the distal tip 1014' and/or the distal sheath 1024', the inflow end 230 of the stent 202 would be in danger of dragging or scraping against the vasculature during delivery. One way to mitigate or eliminate that risk is to provide a distal tip 1014' that is modified compared to distal tip 1014. In particular, distal tip 1014' may include a proximal ring 1015' that is substantially hollow. For example, proximal ring 1015' may have a wall thickness and profile that is generally similar to the wall thickness and profile of the distal sheath 1024', although such one-to-one correspondence is not required. This proximal ring 1015' may be formed as a relatively rigid structure and may receive the terminal inflow end 230 of the stent 202. Preferably, although not absolutely necessarily, this terminal inflow end 230 is also uncovered by the outer cuff 250'. Although provided as merely an example, the proximal ring 1015' may have a length of between about 0.5 mm and about 1.5 mm, including about 1 mm. Typically, the distal tip of a delivery system would include a highly flexible material with an atraumatic tip shape to minimize the likelihood of damaging the vasculature since the distal tip is the leading end of the delivery device. The same may be true of distal tip 1014'. For example, the distal portion of distal tip 1014' may be formed of a first highly flexible material, while the proximal ring 1015' may be formed of a different, rigid material, with the proximal ring 1015' coupled to the distal tip 1014' by any suitable mechanism, including adhesives. In other embodiments, the entire distal tip 1014' may be formed as a highly flexible material, with a rigid ring (e.g., a metal ring or plastic ring or the like) embedded within the proximal end of the distal tip 1014' to form the proximal constraining ring 1015'. In some embodiments, the proximal ring 1015' may be cut from a tube, molded, over-molded, or machined. In some embodiments, the proximal ring 1015' may be joined to the distal tip 1014' via adhesives, overmolding, or a mechanical fit (e.g., a snap fit or crimp connection). In some embodiments, the proximal ring 1015' may be perfectly (or nearly perfectly) cylindrical (e.g., a right cylinder as illustrated). In other embodiments, the proximal ring 1015' may have a slight taper (wider proximally than distally) to allow better re-capture of the inflow end 230 of the stent 202. With the above-described configuration of distal tip 1014' and proximal ring 1015', although much of the annulus section 240 of the prosthetic heart valve 200' is uncovered during delivery, the prosthetic heart valve 200' does not prematurely expand during delivery because a large portion of the outflow end of the prosthetic valve remains constrained by delivery sheath 1024', and the terminal inflow end 230 of the stent 202 remains constrained by proximal ring 1015'. Thus, as should be understood, despite the prosthetic heart valve 200' including an outer cuff 250' (even if the outer cuff 250' is a high-volume outer cuff), the profile of the distal end of the delivery device 1010' (which may be generally referred to as the capsule) does not need to have a larger profile than would be needed for prosthetic heart valve 200 that omits an outer cuff.

As described in connection with the below exemplary delivery and deployment of prosthetic heart valve 200' using delivery device 1010', the outflow portions of the prosthetic heart valve 200' may be deployed in the same manner as would be expected for delivery device 1010. In other words, the distal sheath 1024' may be retracted (e.g., using fine movements via a deployment wheel or actuator similar to deployment wheel 1021) relative to the prosthetic heart valve 200' to remove the constraint that prevents the outflow portions of the prosthetic heart valve 200' from self-expanding. However, because the terminal inflow end 230 of the stent 202 is constrained by proximal ring 1015', the inflow end 230 of the stent 202 may not expand directly as a result of retracting the distal sheath 1024'. In some embodiments, the distal tip 1014' may be "passive" in the sense that it is not capable of translating axially relative to the retainer 1025' that retains the outflow end 232 of the stent 202. In this embodiment, as the distal sheath 1024' is retracted proximally, the middle and/or outflow portions of the prosthetic heart valve 200' begin to self-expand. As this self-expansion occurs, the middle and/or outflow portions of the prosthetic heart valve 200' will begin to axially foreshorten as the prosthetic heart valve 200' expands radially. Eventually, the axial foreshortening will cause the terminal inflow end 230 of the stent 202 to translate proximally with respect to the proximal ring 1015', allowing for complete expansion of the inflow end of the prosthetic heart valve 200. In other embodiments, the distal tip 1014' may be "active" in the sense that it is capable of translating axially relative to the retainer 1025'. With this configuration, when the prosthetic heart valve 200' is in the desired location relative to the native valve annulus, the distal tip 1014' may be advanced distally to uncover the terminal inflow end 230 of the stent 202 to allow it to radially expand, without needing to rely on other portions of the stent axially foreshortening until the terminal end 230 of the stent 202 slips out of the proximal ring 1015'. The "active" configuration may be achieved by any desired means, including a separate shaft that is either interior or exterior to the inner shaft 1026' and is fixed to the distal tip 1014', such that distal or proximal translation of the separate shaft causes corresponding distal or proximal translation of the distal tip 1014' (including proximal ring 1015').

Figure 5A:
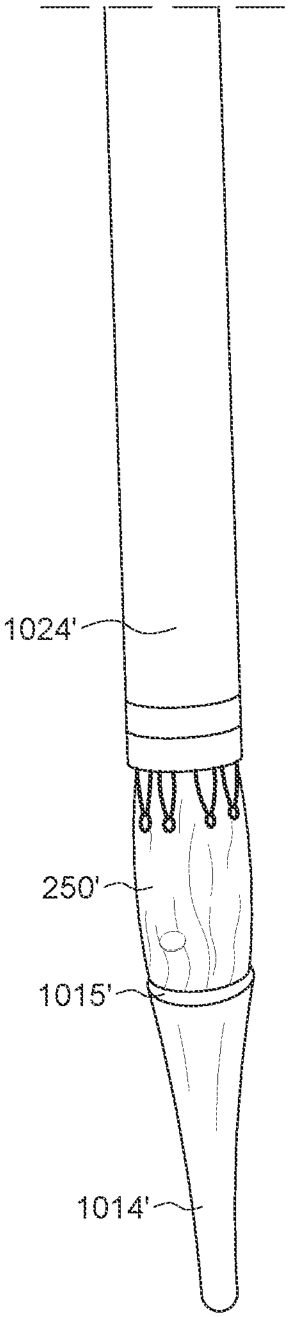
FIG. 5A illustrates the delivery device of FIG. 4 in the delivery condition with the prosthetic heart valve of FIG. 3 loaded therein.

An exemplary use of prosthetic heart valve 200' with delivery device 1010' is described below. Prosthetic heart valve 200' may be transitioned into a collapsed condition over the inner shaft 1026' while the distal sheath 1024' is in the retracted or completely uncovered position. The transitioning may be performed in any suitable fashion, including for example by translating the prosthetic heart valve 200' axially through a funnel to force the prosthetic heart valve 200' to collapse. As the prosthetic heart valve 200' collapses, the retaining elements 218 may be positioned within the corresponding recesses (e.g., female retaining structures) of the proximal retainer 1025'. With the retaining elements 218 positioned within the corresponding recesses of the retainer 1026', the distal sheath 1024' may be advanced distally to cover more and more of the prosthetic heart valve 200' and to retain the prosthetic heart valve 200' in the collapsed condition. If the distal sheath 1024' is incapable of closing the gap distance D, for example because it is simply too short to do so, the distal sheath 1024' may be advanced to its maximum extent which will be at or near the outflow end of the outer cuff 250'. If the distal sheath 1024' is capable of closing some or all of the gap distance D, it may be advanced distally only so far as to the point where it is at or near the outflow end of the outer cuff 250'. If the distal tip 1014' has the "active" configuration, the distal tip 1014' may be in a distally advanced configuration during the above loading steps, and then retracted proximally until the proximal ring 1015' covers the terminal inflow end 230 of the stent 202 to overlie and constrain the terminal inflow end 230 of the stent 202. If the distal tip 1014' has the "passive" configuration, the terminal inflow end 230 of the stent 202 may be manually maneuvered to the inside of the proximal ring 1015'. However, instead of manual maneuvering, in some embodiments of the "passive" configuration, the terminal inflow end 230 of the stent 202 may be pre-constrained by a band, a clamp, or a similar tool before the prosthetic heart valve 200' is drawn into the capsule or distal sheath 1024'. With this embodiment, the axial lengthening that occurs in the middle portion of the stent 202 during radial collapse into the distal sheath 1024' may result in the pre-constrained terminal inflow end 230 being pushed toward or into the proximal ring 1015'. At this point, the band (or clamp or similar tool) may be removed from the terminal inflow end 230 of the stent 202 prior to delivery and deployment of the prosthetic heart valve 200'. Preferably, if the delivery device 1010' has a "fine" and "coarse" mechanism for translating the distal sheath 1024', the "fine" mechanism is used while loading the prosthetic heart valve 200' in the delivery device 1010', although the "coarse" mechanism may be used to initially retract the distal sheath 1024' in preparation for loading the prosthetic heart valve 200' into the delivery device 1010'. After the above steps have been completed, the prosthetic heart valve 200' is in the collapsed delivery condition in the delivery device 1010' and ready for delivery, similar to what is shown in FIG. 5A.

With the system ready for delivery, the distal tip 1014' may be inserted into the patient's vasculature, for example into the femoral artery via a previously placed introducer. In some embodiments, a guidewire may have already been delivered into the patient to a location near or adjacent to the target valve to be replaced, which in this example is the aortic valve. If a guidewire has been delivered already, the distal tip 1014' may be advanced over the guidewire to help guide the delivery device 1010' toward the target site. The delivery device 1010' may be advanced distally through the patient's vasculature, into, through, and around the aortic arch, and back down toward the patient's aortic valve. All the while during delivery, the outer cuff 250' remains entirely (or substantially entirely) uncovered by the distal sheath 1024'.

When the delivery device 1010' is at the desired position relative to the native aortic valve, which may be confirmed by visualization (e.g., fluoroscopy), the prosthetic heart valve 200' may be allowed to expand into the native aortic valve. If the distal tip 1014' has the "active" configuration, it may be first advanced distally to uncover the terminal inflow end 230 of the stent 202. As this occurs, the entire inflow end 230 of the prosthetic heart valve 200', including all (or substantially all) of the outer cuff 250' is uncovered, and these portions may begin to self-expand. Then, the distal sheath 1024' may be retracted (preferably using a "fine" retraction mechanism) to uncover more and more of the prosthetic heart valve 200', allowing for a smooth expansion into the native aortic valve. During expansion, the outer cuff 250' is positioned to press into the native aortic valve annulus to provide enhanced sealing to mitigate PV leak. The valve positioning and/or functionality may be confirmed by visualization before the retaining elements 218 are uncovered by the distal sheath 1024'. If the positioning or function is determined to be suboptimal, the distal sheath 1024' may be advanced to re-collapse the prosthetic heart valve, after which the prosthetic heart valve 200' may be either repositioned for another deployment attempt or removed from the body to abort the procedure. If the valve positioning and function are determined to be suitable, the distal sheath 1024' may be retracted further to uncover the retaining elements 218 to completely release the prosthetic heart valve 200' from its connection to the delivery device 1010'. If included, a resheathing lock (such as resheathing lock 1043) may limit the retraction of the distal sheath 1024' to the point just before uncovering the retaining elements 218, and the resheathing lock may be actuated to allow for the final retraction of the distal sheath 1024' and the final release of the prosthetic heart valve 200'. After complete release, the distal tip 1014' and inner shaft 1026' may be translated proximally through the deployed prosthetic heart valve 200', and the delivery device 1010' removed from the body to complete the procedure.

Figure 5B:
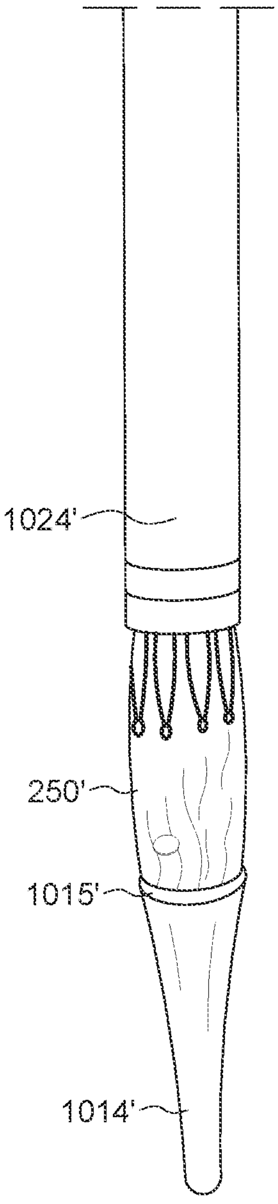
FIGS. 5B-D show the distal sheath of the delivery device being retracted proximally in successive stages after the delivery condition of FIG. 5A
Figure 5C:
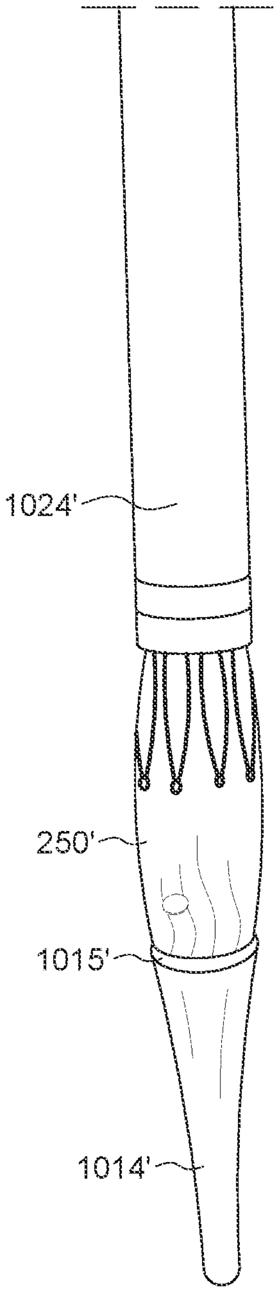
Figure 5D:
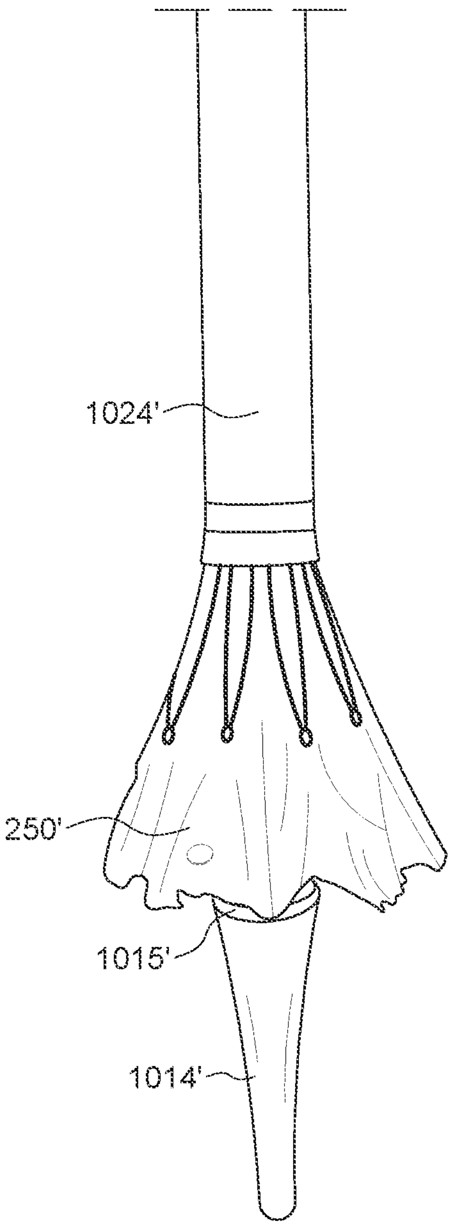

If the distal tip 1014' has the "passive" configuration, instead of starting deployment by advancing the distal tip 1014', deployment may proceed by simply retracting the distal sheath 1024' until the prosthetic heart valve 200' expands (and axially foreshortens) enough for the terminal inflow end 230 of the stent 202 to slip out of the proximal ring 1015'. Other than this step, the remaining deployment of the prosthetic heart valve 200' is the same as described above in connection with the "active" configuration of the distal tip 1014'. FIGS. 5B-D show the distal sheath 1024' being retracted proximally in successive stages after the delivery configuration of FIG. 5A. As shown in FIG. 5D, once the distal sheath 1024' has been retracted far enough, the inflow end portion of the prosthetic heart valve 200' begins to self-expand.

As noted above, although the delivery device 1010' is shown and described in connection with the delivery and deployment of a specific configuration of a prosthetic aortic valve, the delivery device 1010' (with or without suitable modifications) may be used to deliver and deploy other specific configurations of prosthetic heart valves that include outer cuffs (particularly high-volume outer cuffs), as well as using different delivery approaches. For example, the delivery device 1010' may be used for a transseptal delivery of a prosthetic mitral valve with an outer cuff, a transapical delivery of a prosthetic aortic valve with an outer cuff, a transfemoral delivery of a prosthetic tricuspid valve with an outer cuff, etc. If being used as part of a transapical delivery, some of the components may be substantially oriented in the opposite direction. For example, the distal end of the distal sheath may be substantially static, with the terminal inflow end of the prosthetic heart valve being maintained within that distal end of the distal sheath. A distal capsule, which may form part of the distal tip, may cover the outflow end of the prosthetic heart valve up to the outflow end of the outer cuff. During delivery, the outer cuff may be exposed. During deployment, the distal tip may be advanced distally to deploy the valve. Further, although the delivery device 1010' may be most useful with a self-expanding prosthetic heart valve, other types of expandable prosthetic heart valves may be used with delivery device 1010'.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

It will be appreciated that the various dependent claims and the features set forth therein can be combined in different ways than presented in the initial claims. It will also be appreciated that the features described in connection with individual embodiments may be shared with others of the described embodiments.

The invention claimed is:

1. A delivery device for a collapsible prosthetic heart valve, the delivery device comprising:

an inner shaft;

an outer shaft;

a distal sheath disposed entirely distal to the outer shaft and about a portion of the inner shaft to form a compartment with the inner shaft, the compartment being sized to receive the prosthetic heart valve, the inner shaft and the distal sheath being axially translatable relative to one another; and a distal tip disposed at a distal end of the delivery device;

wherein the distal sheath is translatable between a proximal-most position and a distal-most position, the compartment being completely exposed when the distal sheath is in the proximal-most position, and a gap distance existing between an entire circumference of a distal-most end of the distal sheath and a proximal-most end of the distal tip when the distal sheath is in the distal-most position.

2. The delivery device of claim 1, wherein the distal tip includes a distal portion and a proximal portion, the distal portion having a rigidity that is less than a rigidity of the proximal portion.

3. The delivery device of claim 2, wherein the proximal portion of the distal tip is ring-shaped.

4. The delivery device of claim 3, wherein the proximal portion of the distal tip has an outer diameter that is equal to an outer diameter of the distal sheath.

5. The delivery device of claim 3, wherein the proximal portion of the distal tip has a wall thickness that is equal to a wall thickness of the distal sheath.

6. The delivery device of claim 1, further comprising a retainer positioned at a proximal end of the compartment, the retainer being configured to mate with retaining elements of the prosthetic heart valve.

7. The delivery device of claim 6, wherein the distal tip is axially fixed relative to the retainer.

8. The delivery device of claim 6, wherein the distal tip is axially translatable relative to the retainer.

9. A prosthetic heart valve system comprising:
- a prosthetic heart valve, including:
  - a self-expanding frame;
  - a valve assembly mounted within the frame; and
  - an outer cuff on an outer surface of the frame; and
- a delivery device, including:
  - an inner shaft;
  - an outer shaft;
  - a distal sheath disposed distal to the outer shaft and about a portion of the inner shaft to form a compartment with the inner shaft, the inner shaft and the distal sheath being axially translatable relative to one another; and
  - a distal tip disposed at a distal end of the delivery device;
- wherein the system has a delivery condition in which the distal sheath is in a distal-most position in which the distal sheath overlies portions of the prosthetic heart valve but a distal end of the distal sheath leaves the outer cuff uncovered.

10. The prosthetic heart valve system of claim 9, wherein in the delivery condition, a gap distance exists between the distal end of the distal sheath and a proximal end of the distal tip, the outer cuff being positioned along the gap distance.

11. The prosthetic heart valve system of claim 9, wherein the distal tip includes a distal portion and a proximal portion, the distal portion having a rigidity that is less than a rigidity of the proximal portion.

12. The prosthetic heart valve system of claim 11, wherein the proximal portion of the distal tip is ring-shaped.

13. The prosthetic heart valve system of claim 12, wherein in the delivery condition of the system, a terminal inflow end of the prosthetic heart valve is positioned within the proximal portion of the distal tip.

14. The prosthetic heart valve system of claim 13, wherein the delivery device includes a retainer, and in the delivery condition of the system, retaining elements at an outflow end of the prosthetic heart valve are coupled to the retainer.

15. The prosthetic heart valve system of claim 14, wherein the distal tip is axially fixed relative to the retainer.

16. The prosthetic heart valve system of claim 14, wherein the distal tip is axially translatable relative to the retainer.

17. A method of implanting a prosthetic heart valve into a patient, the method comprising:
- transitioning a prosthetic heart valve into a collapsed delivery condition within a compartment of a delivery device, the prosthetic heart valve having a self-expanding frame, a valve assembly mounted within the frame, and an outer cuff on an outer surface of the frame, the delivery device including an inner shaft, and outer shaft, a distal sheath disposed distal to the outer shaft and about a portion of the inner shaft to form the compartment with the inner shaft, and a distal tip disposed at a distal end of the delivery device;
- delivering the prosthetic heart valve into a vasculature of the patient while the prosthetic heart valve is in the collapsed delivery condition in which the distal sheath is in a distal-most position in which the distal sheath overlies portions of the prosthetic heart valve but a distal end of the distal sheath leaves the outer cuff uncovered, the outer cuff of the prosthetic heart valve being uncovered by the delivery device during the delivering;
- positioning the prosthetic heart valve within or adjacent to a native heart valve annulus while the prosthetic heart valve is in the collapsed delivery condition; and
- while the prosthetic heart valve is positioned within or adjacent to the native heart valve annulus, retracting the distal sheath relative to the inner shaft of the delivery device to allow the prosthetic heart valve to expand so that the outer cuff contacts that native valve annulus.

18. The method of claim 17, wherein the distal tip includes a proximal ring-shaped portion, and during the delivering, a terminal inflow end of the prosthetic heart valve is received within and constrained by the proximal ring-shaped portion of the distal tip.

19. The method of claim 18, wherein while the prosthetic heart valve is positioned within or adjacent to the native heart valve annulus, and before retracting the distal sheath, advancing the distal tip distally to uncover the terminal inflow end of the prosthetic heart valve.

20. The method of claim 18, wherein while retracting the distal sheath, the terminal inflow end of the prosthetic heart valve slips out of the proximal ring-shaped portion of the distal tip without distal advancement of the distal tip.

* * * * *